United States Patent [19]

Ohlinger et al.

[11] Patent Number: 4,581,174

[45] Date of Patent: Apr. 8, 1986

[54] PROCESS FOR THE CONTINUOUS PREPARATION OF ORGANIC MONO-AND/OR POLYISOCYANATES

[75] Inventors: Rainer Ohlinger, Heidelberg; Harald Schnez, Neustadt; Ludwig Pfannenstiehl, Kirchheimbolanden; Bernd Blumenberg, Frankenthal; Hans J. Raabe, Wachenheim, all of Fed. Rep. of Germany

[73] Assignee: BASF Aktiengesellschaft, Ludwigshafen, Fed. Rep. of Germany

[21] Appl. No.: 695,196

[22] Filed: Jan. 25, 1985

[30] Foreign Application Priority Data

Jan. 31, 1984 [DE] Fed. Rep. of Germany ....... 3403204

[51] Int. Cl.$^4$ ............................................ C07C 118/02
[52] U.S. Cl. .................................................... 560/347
[58] Field of Search ................................. 260/453 PH

[56] References Cited

U.S. PATENT DOCUMENTS 4,128,569 12/1978 Horn et al. ................... 260/453 PH

*Primary Examiner*—Dolph H. Torrence
*Attorney, Agent, or Firm*—Joseph D. Michaels

[57] ABSTRACT

The invention relates to a process for the continuous preparation of organic isocyanates, preferably polyisocyanates, through the reaction of organic amines, preferably polyamines, with phosgene in the presence of organic solvents under pressure, for example from 5 to 100 bar, at elevated temperatures, for example from 100 to 220° C., whereby the reaction mixture is partially recycled, preferably using natural circulation, and the hydrogen chloride content in the reaction mixture prior to the addition of the amine is less than 0.5 percent by weight based on the total weight of the reaction mixture and the molar ratio of phosgene to NH$_2$ group in the organic amines is from 12:1 to 200:1.

9 Claims, 1 Drawing Figure

PROCESS FOR THE CONTINUOUS PREPARATION OF ORGANIC MONO-AND/OR POLYISOCYANATES

BACKGROUND OF THE INVENTION

1. Field of the Invention

This invention pertains to a continuous process for the preparation of organic isocyanates.

2. Description of the Prior Art

The manufacture of isocyanates from primary amines and phosgene has been disclosed. Depending on the nature of the amines, the reaction is carried out either in the gas phase or in the liquid phase, either batchwise or continuously (W. Siefken, Liebigs Ann. 562, 75 (1949).

The conventional processes suffer from numerous disadvantages. If low temperatures are used for the initial phosgenation (cold phosgenation), the liberation of large amounts of phosgene during heating the reaction mixture to the final phosgenation temperature (hot phosgenation temperature) presents a problem which is difficult to deal with and which is further aggravated by the high toxicity of phosgene. Low temperature processes also suffer from a further disadvantage, namely that the rate of reaction is relatively low, so that large reaction volumes have to be handled. In the two-stage processes, the end product and the carbamoyl chloride formed as an intermediate in the first stage can react with some of the starting amine to form substituted ureas and polyureas or other undesirable products.

In a different continuous process for the preparation of isocyanates, a portion of the reaction solution is recycled at elevated pressure and elevated temperature. As disclosed in Federal Republic of Germany application No. 1,037,444 (U.S. Pat. No. 2,822,373), the phosgene solution here is mixed with an amine solution before entering the reaction vessel. Here, a certain turbulence must be generated at the point where the two solutions meet, however, the flow tube can easily become clogged, so that turbulence is no longer possible.

Federal Republic of Germany Pat. No. 1,175,666 (United Kingdom Pat. No. 827,376) discloses a process for the continuous preparation of isocyanates at elevated pressure in a reaction tube whereby the starting components are introduced into the reaction tube at a pressure exceeding 3 bar, are then reacted with increasing temperature, and the reaction mixture is drawn off through a relief valve at the end of the reaction tube to obtain the isocyanates. Since the recycled phosgene has not been subjected to hydrogen chloride purification, salts are formed and deposits build up on the mixing nozzle.

In order to improve this process, Federal Republic of Germany application No. 1,593,412 (United Kingdom No. 1,146,656 and United Kingdom No. 1,141,910) disclose the decomposition of the carbamoyl chloride into isocyanate and hydrogen chloride and the removal of the hydrogen chloride and excess phosgene from the reaction mixture in a distillation column at temperatures from 120° to 180° C. and at a pressure of from 10 to 50 bar, with the phosgene being refluxed.

Federal Republic of Germany published application No. 19 56 777 (U.S. Pat. No. 3,781,320 and U.S. Pat. No. 3,887,167) disclose a mixing device comprised of a chamber and a coaxially positioned rotor equipped with blades, the ends of which are positioned close to the interchamber wall, for the preparation of organic isocyanates in a one-step process. According to this publication, it is not necessary to remove hydrogen chloride from the reaction mixture since its presence does not adversely affect the process.

According to the disclosure of U.S. Pat. No. 3,829,458, organic isocyanates are manufactured continuously from primary organic amines and phosgene in an inert organic solvent in one or more packed reaction vessels, preferably with recycling of the reaction mixture, under conditions of what is called transition flow. Using this relatively simple process isocyanates can be manufactured with a high volume-to-time yield. However, in this process the introduction of the amines into the phosgene-containing reaction solution again presents certain difficulties, since with some amines optimum intermixing of the starting components can only be achieved with difficulty. If, on the other hand, the reactants are not intermixed adequately, amine hydrochlorides and ureas are formed as by-products; these in part deposit on the packing and can lead to blockage of the packed columns.

A series of known preparation methods has resulted in significant technological successes, however, all these methods have the disadvantage that excess amounts of polymers and other undesirable by-products are formed. The formation of such by-products can significantly reduce the isocyanate yield or the quality of the product.

Good results are also obtained with the process described in Federal Republic of Germany published application No. 26 24 285 (U.S. Pat. No. 4,128,569). Here the phosgene is mixed into the reaction solution, which itself is cycled in a loop and the resulting reaction mixture and the amines or amine solution is fed into the mixing and reaction zone in such a way that in this zone an energy dissipation density of from 5 to 1000 kJ is produced per $m^3$ recycled reaction mixture plus added amine solution. However, the desired phosgenation quality also cannot be achieved with this process, especially with respect to the formation of by-products.

The objective of the invention at hand was to improve the mixing processes for the continuous preparation of isocyanates, especially the process of Federal Republic of Germany published application No. 26 24 285 and to completely, or at least partially, eliminate existing defects.

SUMMARY OF THE INVENTION

This objective was unexpectedly met by reducing the hydrogen chloride content and increasing the phosgene content in the reaction mixture.

Hence, the subject of the invention is a process for the continuous preparation of organic isocyanates by reacting organic amines with phosgene in the presence of organic solvents under pressure at elevated temperature, whereby the reaction mixture is partially recycled in a loop, wherein the hydrogen chloride content in the reaction mixture prior to the addition of the amine is less than 0.5 percent by weight, preferably from 0.01 to 0.4 percent by weight based on the total weight of the reaction mixture and wherein the molar ratio of phosgene to $NH_2$ group in the organic amines is from 12:1 to 200:1.

The process of the invention advantageously avoids the intermediate formation of a salt and essentially suppresses by-product formation, thereby increasing the isocyanate concentration in the reactor. This results in an energy savings when the resulting reaction mixture is further processed. Compared to the typical cascade process, the phosgenation reactor can be reduced in size, thus increasing the volume-to-time yield. The resulting hydrogen chloride gas is separated by means of rectification at high pressure.

DESCRIPTION OF THE PREFERRED EMBODIMENTS

Figure 1:
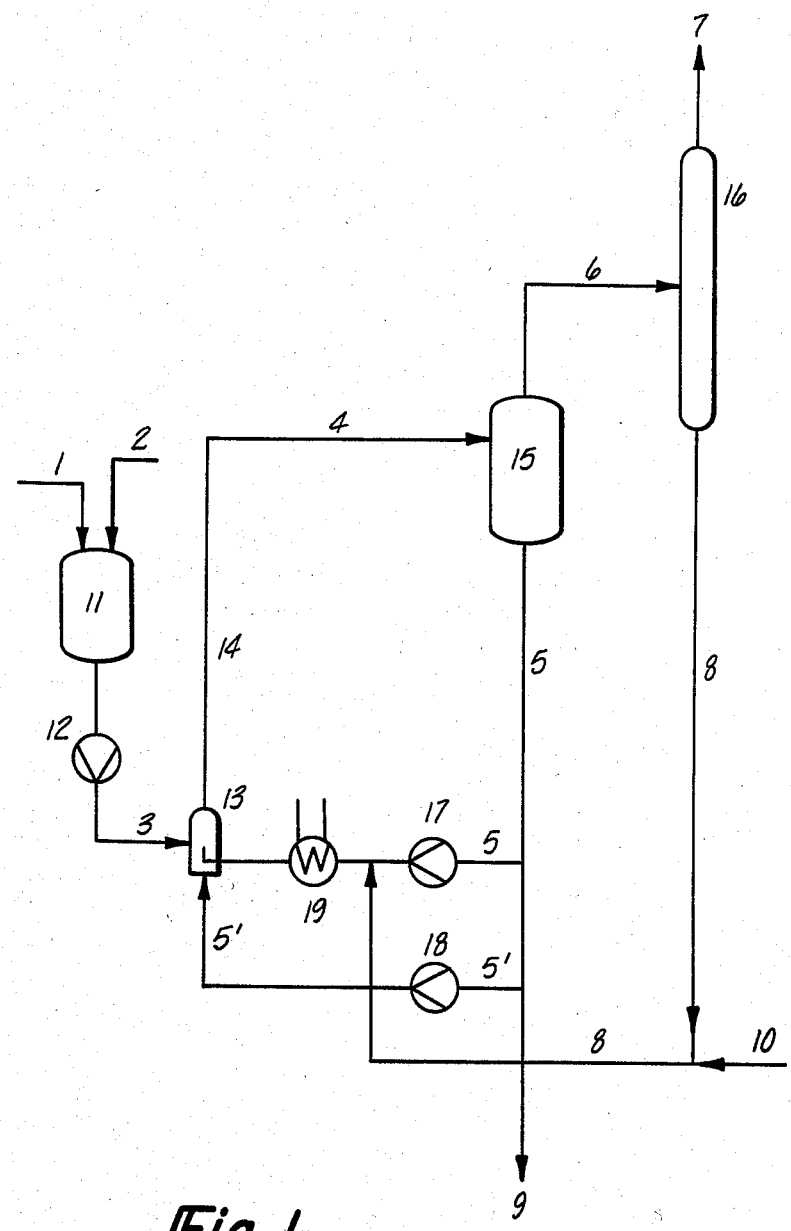
FIG. 1 is a line representation of a reactor system suitable for performing this invention.

The process according to the invention is quite generally applicable to the manufacture of organic isocyanates which can be obtained by reacting amines with phosgene. For example, monoisocyanates, diisocyanates and/or polyisocyanates can be manufactured from the corresponding organic monoamines, diamines and polyamines.

Suitable organic monoamino compounds have the formula R—$NH_2$, where R is an unsubstituted or substituted monofunctional aliphatic, cycloaliphatic or, preferably, aromatic radical having 1 to 20, preferably 6 to 12, carbon atoms. Examples are aliphatic monoamines, e.g., methylamine, ethylamine, butylamine, octylamine and stearylamine, cycloaliphatic monoamines, e.g., cyclohexylamine, and especially aromatic monoamines, e.g., aniline, toluidines, naphthylamines, chloroanilines and anisidines.

Preferably, however, the diisocyanates and polyisocyanates, which are of importance for the industrial manufacture of polyurethanes, are manufactured from the corresponding diamines and polyamines by the new process. Suitable diamino compounds have the formula $H_2N$—R'—$NH_2$, where R' is a difunctional aliphatic or cycloaliphatic radical having 2 to 18, preferably 4 to 12 carbon atoms or, preferably, is a functional aromatic radical which consists of one or more aromatic rings having from 6 to 18 carbon atoms directly linked to one another or linked via divalent bridge members, e.g., —O—, —$SO_2$—, —$CH_2$— and

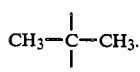

The diamino compounds and/or polyamino compounds may be used individually or as mixture.

Said aliphatic, cycloaliphatic, or, preferably, aromatic diamino compounds are, for example: 1,4-diaminobutane, 1,6-diaminohexane, 1,10-diaminodecane, 1,12-diaminododecane, 1,4- or 1,3-diaminocyclohexane, 4,4'-diaminodicyclohexyl, 4,4'-, 2,4'-, 2,2'-diaminodicyclohexylmethane, 3,3'-dimethyl-4,4'-diaminodicyclohexylmethane, 4,4'-diaminodiphenyl-, 1,4- or 1,3-diphenylenediamine, 1,5- or 1,8-naphthylenediamine, 2,4- or 2,6-toluenediamine, and 2,2'-, 2,4'- or 4,4'-diaminodiphenylmethane.

Examples of suitable polyamines are tri(p-aminophenyl)methane, 2,4,6-triamino-toluene and condensation products which are obtained from substituted or unsubstituted aniline derivatives and aldehydes or ketones in the presence of acids, e.g., polyphenyl-polymethylene-polyamines.

Preferable organic amines are: 1,6-hexamethylenediamine, mixtures of 1,6-hexamethylene, 2-methyl-1,5-pentamethylene, and 2-ethyl-1,4-butylenediamine, 3-aminomethyl-3,5,5-trimethylcyclohexylamine, 2,4'-, 4,4'-, 2,2'-diaminodiphenylmethane, or mixtures of at least two of the cited isomers, 2,4- and 2,6-toluenediamine or their mixtures, polyphenyl-polymethylene-polyamines or mixtures of diaminodiphenylmethanes and polyphenyl-polymethylenepolyamines.

The process according to the invention is particularly suitable for the manufacture of aromatic diisocyanates and/or polyisocyanates from the corresponding amines and is therefore preferentially used for this purpose.

Gaseous and/or, preferably, liquid phosgene is used as the other initial component. The liquid phosgene can be reacted as such or when diluted with a solvent suitable for dephosgenation, for example, monochlorobenzene, dichlorobenzene, xylene, toluene, etc. The molar ratio of amine-to-phosgene is advantageously proportioned such that from 12 to 200 moles phosgene, preferably from 12 to 98 moles, and more preferably from 40 to 80 moles, is present in the reaction mixture per $NH_2$ group.

Suitable inert organic solvents are compounds in which the amines and the phosgene are at least partially soluble.

Chlorinated aromatic hydrocarbons, e.g., chlorobenzene, o-dichlorobenzene, p-dichlorobenzene, trichlorobenzenes, the corresponding chloro-toluenes and xylenes, chloroethylbenzene, monochlorodiphenyl, α- and β-naphthyl chloride, alkyl benzoates, and dialkyl phthalates, e.g., diethyl isophthalate, toluene and xylenes have proved particularly suitable. The solvents may be used individually or as mixtures. Advantageously, the solvent used has a lower boiling point than the isocyanate to be manufactured, so that the solvent can readily be separated from the isocyanate by distillation. The amount of solvent is advantageously such that the reaction mixture has an isocyanate content of from 2 to 40 percent by weight, preferably from 5 to 20 percent by weight, based on the total weight of the reaction mixture.

The amines may be used undiluted or as solutions in organic solvents. In particular, amine solutions with an amine content of from 5 to 50 percent by weight, preferably from 15 to 35 percent by weight, based on the total weight of the solution, are used.

The reaction is advantageously carried out at from 100° to 220° C., preferably from 120° C. to 180° C., and at pressures of from 5 to 100 bars, preferably from 15 to 50 bars. The temperature used in the process according to the invention is above the decomposition point of the carboamoyl chloride formed as an intermediate product of the reaction of phosgene with amine. The only upper limits on the pressure are set by technical considerations and, at times, safety considerations, but higher pressures than those stated do not produce any further increase in yield. The rectification of the separated hydrogen chloride is, however, significantly easier at high pressure.

In order to perform the process of the invention, the reaction mixture, which is comprised of a solvent, dissolved isocyanate, phosgene, hydrogen chloride, as well as phosgenation by-products, is cycled in a loop, preferably in a pressurized mixing loop, by means of a circulating pump or, preferably, by means of natural circulation, whereby the recycled reaction mixture is introduced into the mixing and reaction zone, partially via a pump and nozzle. Fresh phsogene and, in some cases, solvent-containing phosgene is added to the reaction mixture through the circulating stream, whereby in a preferred embodiment of the process the fresh phosgene, preferably in liquid form, together with the recycled and purified phosgene from the hydrogen chloride removal step is incorporated into the partial stream of the reaction mixture which is directed through the nozzle. The amine, or preferably the amine solution, is introduced into the reaction mixture through the nozzle. A stream of the reaction mixture, which corresponds in volume to the total liquid charge, is removed from the loop as a product solution in order to further process and isolate the isocyanate. In order to remove the hydrogen chloride released during phosgenation, a gas removal chamber is required in the loop. With the aid of this chamber, the hydrogen chloride content in the reaction mixture prior to the addition of the amine can be lowered to less than 0.5 percent by weight, preferably from 0.01 to 0.4 percent by weight, and more preferably from 0.1 to 0.3 percent by weight based on the total weight of the reaction mixture.

If the reaction mixture is circulated by means of natural circulation, it is desirable that the cylindrically shaped portion of the equipment, which is located between the nozzle and the gas removal chamber and in which the loop stream rises vertically, possess a length of from 5 to 25 m, preferably from 10 to 15 m, and have an inner diameter which is nearly independent of said length and which is from 5 to 150 cm, preferably from 10 to 100 cm. The circulating pump (18) shown on the drawing can then be eliminated.

The reaction mixture, which is continually purified of hydrogen chloride, then preferably contains per 100 parts by weight reaction mixture from 9.5 to 86, preferably from 40 to 50 parts by weight solvent, from 4 to 40, preferably from 20 to 30 parts by weight organic isocyanate, from 10 to 50, preferably from 20 to 40 parts by weight phosgene, and from 0.01 to 0.5, preferably from 0.01 to 0.4 parts by weight hydrogen chloride.

The volume of the reaction loop is dimensioned such that the mean residence times can be adjusted from approximately one minute to one hour, preferably from five minutes to 0.5 hours, based on the volumetric flow of the discharged product solution.

The amount of reaction mixture maintained in the circulating loop should be such that the volumetric ratio of the total amount of reaction mixture circulating in the loop plus the added phosgene, plus, in some cases, the added solvent-containing phosgene relative to the amount of amine solution added is from 300:1 to 1:1, preferably from 100:1 to 5:1.

The concentration of the reaction mixture comprised of the reaction mixture circulated in the loop, the added phosgene, and the optionally added solvent-containing phosgene, which is directed through the nozzle, can be from 5 to 100 percent by weight, preferably from 10 to 50 percent by weight of the total reaction mixture located in the reaction loop. In extreme cases, the entire reaction mixture can be passed through the nozzle. The portion of the reaction mixture which is passed through the nozzle is highly accelerated so that it leaves the nozzle as a jet with a high relative velocity compared to the contents of the reaction tube. By adding the amine solution in the vicinity of the nozzle outlet, it is intensively mixed with the reaction mixture in an extremely short time.

In order to achieve optimum reaction rates and optimum yields of isocyanate it is essential to the invention that an energy dissipation density of from 5 to 1000, preferably from 50 to 400 kJoule per $m^3$ of recycled reaction mixture plus amine feed solution prevail in the mixing and reaction zone. This energy dissipation density is generated if the part of the reaction mixture which passes through the nozzle is fed to the mixing and reaction zone at a nozzle exit velocity of from 1 to 60 m/sec., preferably from 20 to 40 m/sec., and the amine or the amine solution is fed to the mixing and reaction zone through the amine feed pipe with an exit velocity of from 0.3 to 30 m/sec., preferably from 0.5 to 20 m/sec. The mixing and reaction zone is characterized by the accelerated mass flow of the recycled reaction mixture and the amine solution fed in, and the combined liquid streams must exhibit the above energy dissipation densities. The mixing and reaction zone has a mean diameter which corresponds to from 3 to 30 times, preferably from 10 to 25 times, the mean diameter of the drive jet of the reaction mixture. The mean diameter of the drive jet means the diameter of a circle of equal area to that of the cross-sectional areas of the nozzle orifices, for example, of annular nozzles or slot nozzles, of the mixing zone. The mixing and reaction zone may be of constant cross-section or the cross-section may alter in the direction of flow. The said zone can have various shapes, the shape advantageously being suited to the shape of nozzle used. In general, conical segments or, preferably, cylindrical tubes are used. In the latter case the length should be from 1 to 20 times, preferably from 1.5 to 5 times, the diameter. If the mixing and reaction zone does not have a circular cross-section, of if cross-section is not constant over its length, the length of the zone should be from 1 to 20 times, preferably from 1.5 to 5 times, the hydraulic diameter. This latter term means the diameter of a cylindrical tube which, at equal throughput and equal length, results in the same pressure loss as the mixing and reaction zone in question.

The mixing and reaction zone is part of the reaction loop, the size of which is characterized by the above mean residence times. The reaction chamber need not necessarily be constructed as a separate reaction vessel but can instead, for example, also be constructed as a reaction tube and form part of the recycle pipeline system.

The venting space which allows the hydrogen chloride formed during the phosgenation to escape is advantageously, but not necessarily, located above the reaction chamber. If a separate reaction vessel is used as the reaction chamber, it is advantageous to use the upper part of this vessel as the venting space and to withdraw the hydrogen chloride gas, containing phosgene and solvent vapors, at that point. Instead, it is however also possible to provide a separate venting vessel in the recycling system, downstream from the reaction chamber.

A preferred embodiment of the process of manufacture according to the invention is explained once again, in greater detail, with reference to the accompanying drawing.

| | |
|---|---|
| 1 | Feed line for amine |
| 2 | Feed line for solvent |
| 3 | Feed line for amine-containing solvent |
| 4 | Recycling line for reaction mixture |
| 5 | Recycling line for the reaction mixture recycled through the (jet) nozzle |
| 5' | Recycling line for recycled reaction mixture |
| 6 | Discharge line for hydrogen chloride, phosgene, and solvent vapors |
| 7 | Discharge line for hydrogen chloride |
| 8 | Return line for phosgene and condensed solvent |
| 9 | Discharge line for product solution to isolate the |

-continued

| | | |
|---|---|---|
| | isocyanate | |
| 10 | Feed line for phosgene | |
| 11 | Mixing vessel | |
| 12 | Metering pump | |
| 13 | Nozzle (jet nozzle) | |
| 14 | Mixing and reaction zone | |
| 15 | Gas removal chamber | |
| 16 | Rectification column | |
| 17 | Recycling pumps | |
| 18 | Recycling pumps | |
| 19 | Heat exchanger | |

The reaction mixture is circulated through feed lines 4, 5, and 5', which must be filled with at least enough reaction mixture to assure that the jet nozzle 13 is fully immersed in the reaction mixture, through the circulating pump 17, the heat exchanger 19, and the jet nozzle 13 as well as, optionally, the circulating pump 18 whereby solvent-containing phosgene is optionally added to the reaction mixture through feed line 8 and fresh phosgene is optionally added to the reaction mixture through feed line 10 and return line 8. The reaction mixture in recirculating line 5 is divided into partial streams 5' and 5. Partial stream 5 is enriched with fresh and recycled phosgene and is fed into the reaction mixture directly through circulating line 5, circulating pump 17, and heat exchanger 19 and is injected into the reaction mixture at high acceleration in the form of a jet, while the isocyanate-containing reaction mixture is removed from the other partial stream through recirculating line 5' via discharge line 9. Amine is fed into mixing vessel 11 through feed line 1, and solvent is fed into mixing vessel 11 through feed line 2. The amine solution is fed into feed line 3 via metering pump 12, intensively mixed with the reaction mixture in the mixing and reaction zone 14, and is reacted. The volatile components, namely hydrogen chloride, partially excess phosgene, and solvent vapors, are released from gas removal chamber 15 through discharge line 6 into rectification column 16. There the solvent and phosgene is purified and then introduced to the reaction mixture through return line 8, while the gaseous hydrogen chloride is drawn off through discharge line 7. The isocyanate-containing reaction mixture prepared according to the process of the invention is drawn off through the discharge line for the product solution 9 and is further processed with the aid of conventional purification methods to produce isocyanates.

The process of the invention is further explained in the following examples.

EXAMPLES 1-5

The setup of the process is shown in the figure. A reaction tube of 100 mm diameter and having a volume of 160 l was used as the pressurized mixing loop 4, 5, 5'. The gas removal chamber consisted of a 100 l vessel filled from 5 to 60 percent by volume with the reaction mixture. The reaction mixture was circulated through circulating lines 4, 5, and 5' by means of natural circulation. Circulating pump 18 was therefore not necessary. The added fresh liquid phosgene was mixed with recycled phosgene and was reincorporated with the reaction mixture through return line 8 between circulating pump 17 and heat exchanger 19. The reaction mixture in circulating line 5 was accelerated using a rotary-type pump and was injected into the reaction mixture by means of a jet nozzle having an inside diameter of from 6 to 16 mm. The amine solution was incorporated into the jet through a feed line having a diameter of from 2 to 4 mm. At the beginning of the reaction phosgene-saturated monochlorobenzene is charged into the pressurized mixing loop.

The amines used to prepare the isocyanates, the flow rates, reaction conditions, and test results are summarized in the following table.

TABLE

| Example | 1 | 2 | 3 | 4 | 5 |
|---|---|---|---|---|---|
| Diameter of jet (mm) | 10 | 10 | 10 | 10 | 10 |
| Diameter of amine feed line (mm) | 4 | 4.5 | 3.5 | 4 | 4 |
| Liquid volume in pressurized mixing loop (l) | 500 | 600 | 700 | 500 | 800 |
| Amine | Polymeric MDA | Polymeric MDA | DIPPA | TDA | HMDA |
| Amine content in base wolution (wt. %) | 30 | 25 | 34 | 22 | 10 |
| Temperature of base solution (°C.) | 170 | 127 | 136 | 170 | 185 |
| Base solution feed rate 3 (kg/hr.) | 500 | 295 | 542 | 460 | 400 |
| Phosgene feed rate 10 (kg/hr.) | 150 | 76 | 100 | 114 | 70 |
| Flow rate of recycling mixture ($M^3$/hr) | 30 | 36 | 24 | 28 | 22 |
| Throughput through jet nozzle 13 ($m^3$/hr) | 8 | 3.5 | 4.5 | 6 | 7 |
| Linear velocity of jet (m/sec.) | 28 | 12 | 16 | 21 | 24.8 |
| Velocity of amine addition (m/sec.) | 11 | 5 | 15 | 10 | 8.9 |
| Temperature in pressurized mixing loop (°C.) | 130 | 123 | 120 | 130 | 180 |
| Pressure in pressurized mixing loop (bar) | 14.5 | 11 | 12 | 14.5 | 24.8 |
| Composition of the reaction mixture after joining return line 8 per 100 parts by weight | | | | | |
| Monochlorobenzene (wt. pts.) | 41.4 | 52.4 | 32 | 41.5 | 60 |
| Isocyanate (wt. pts.) | 19.5 | 12.3 | 29.7 | 19 | 5 |
| Phosgene (wt. pts.) | 38.6 | 35.0 | 38 | 39 | 35 |
| Hydrogen chloride (wt. pts.) | 0.4 | 0.25 | 0.3 | 0.45 | 0.1 |
| Pressure in feed line 5 downstream from heat exchanger and ahead of jet nozzle (bar) | 20.5 | 15.5 | 16.5 | 19 | 29.4 |
| Solvent-phosgene return 8 from rectification column 16: 85% $COCl_2$ (kg/hr.) | 610 | 380 | 620 | 560 | 650 |
| Operation time (hr.) | 1400 | 48 | 170 | 120 | 72 |
| Yield (%) | 100 | 100 | 99.5 | 96 | 92 |

TABLE-continued

| Example | 1 | 2 | 3 | 4 | 5 |
|---|---|---|---|---|---|
| Isocyanate | Polymeric MDI | Polymeric MDI | DIPPI | TDI | HMDI |

Explanation of Symbols in Table:
Polymeric MDA: Mixture of diphenylmethanediamines and polyphenyl polymethylene polyamines.
Polymeric MDI: Mixture of diphenylmethane diisocyanates and polyphenyl polymethylene polyisocyanates having an isocyanate content of 31 percent by weight
DIPPA: 2,6-diisopropyl-1-phenylamine
DIPPI: 2,6-diisopropyl-1-phenyl isocyanate
TDA: Mixture of 2,4- and 2,6-toluenediamine in an 80:20 weight ratio
TDI: Mixture of 2,4- and 2,6-toluenediisocyanate in an 80:20 weight ratio
HMDA: 1,6-hexamethylenediamine
HMDI: 1,6-hexamethylenediisocyanate
Drawing The embodiments of the invention in which an exclusive privilege or property is claimed are defined as follows:

1. A process for the continuous preparation of organic isocyanates through the reaction of organic amines with phosgene in the presence of organic solvents under pressure from 15 to 50 bars at elevated temperatures, whereby the reaction mixture is partially recirculated in a loop, wherein the hydrogen chloride content in the reaction mixture prior to the addition of the amine is less than 0.5 weight percent based on the total weight of the reaction mixture and the molar ratio of phosgene to $NH_2-$ groups in the organic amines is from 12:1 to 200:1.

2. The process of claim 1 wherein the hydrogen chloride content in the reaction mixture is from 0.01 to 0.4 weight percent, based on the total weight of the reaction mixture.

3. The process of claim 1 wherein the reaction is performed in a compression mixing loop.

4. The process of claim 1 wherein the reaction mixture is circulated as a result of differing densities in the loop.

5. The process of claim 1 wherein the reaction temperature is 100° to 220° C.

6. The process of claim 1 wherein 100 weight parts of the recycled reaction mixture contain: 9.5 to 86 weight parts organic solvent, 4 to 40 weight parts organic isocyanate, 10 to 50 weight parts phosgene, and 0.01 to 0.5 weight parts hydrogen chloride.

7. The process of claim 1 wherein the volumetric ratio between the total amount of added phosgene, the added solvent-containing phosgene, and the reaction mixture in circulation relative to the amount of amine or amine solution added is from 300 to 1:1.

8. The process of claim 1 wherein the type of organic amine is selected from the group consisting of aliphatic, cycloaliphatic, aliphatic-aromatic, aromatic mono-, di- and polyamines.

9. The process of claim 1 wherein the organic amine reacted is selected from the group consisting of 1,6-hexamethylenediamine; mixtures of 1,6-hexamethylene-, 2-methyl-1,5-pentamethylene-, and 2-ethyl-1,4-butylenediamine; 3-aminomethyl-3,5,5-trimethylcyclohexylamine; 2,4'-, 4,4'-, 2,2'-diaminodiphenylmethane, and mixtures of at least two of the above-cited isomers: 2,4- and 2,6-toluenediamine and their mixtures; polyphenyl polymethylene polyamines; and mixtures of diaminodiphenylmethanes and polyphenyl polymethylene polyamines.

* * * * *